United States Patent [19]

Chun et al.

[11] 4,258,063

[45] Mar. 24, 1981

[54] SELF-EMULSIFYING COSMETIC BASE

[75] Inventors: Ho-Ming Chun, New Brighton; Allan L. Melby, Andover, both of Minn.

[73] Assignee: Henkel Corporation, Minneapolis, Minn.

[21] Appl. No.: 918,260

[22] Filed: Jun. 23, 1978

[51] Int. Cl.$^3$ .............................................. A61K 7/48
[52] U.S. Cl. ...................................... 424/365; 424/70
[58] Field of Search ........................ 424/365, 172, 319

[56] References Cited

U.S. PATENT DOCUMENTS

| | | | |
|---|---|---|---|
| 2,468,012 | 4/1949 | Isbell | 252/546 |
| 2,814,643 | 11/1957 | Aelony | 562/553 |
| 2,816,920 | 12/1957 | Andersen | 562/553 |
| 2,876,259 | 3/1959 | Nordgren | 562/571 |
| 2,895,989 | 7/1959 | Sexton | 562/571 |
| 2,929,788 | 3/1960 | Freese et al. | 252/546 X |
| 3,024,197 | 3/1962 | Dohr et al. | 252/546 |
| 3,093,591 | 6/1963 | Freese et al. | 252/546 |
| 3,430,641 | 3/1969 | Newman | 562/571 |
| 3,533,955 | 10/1970 | Pader et al. | 252/546 |
| 3,534,032 | 10/1970 | Kalopissis et al. | 252/546 |
| 3,553,141 | 1/1971 | Katsumi et al. | 252/546 |
| 4,026,818 | 5/1977 | Ciaudelli | 424/172 X |
| 4,035,513 | 7/1977 | Kumano | 424/172 |
| 4,045,550 | 8/1977 | Kelly et al. | 424/172 X |
| 4,062,976 | 12/1977 | Michaels | 424/319 |
| 4,076,799 | 2/1978 | Weller et al. | 434/329 |

FOREIGN PATENT DOCUMENTS

| | | | |
|---|---|---|---|
| 615481 | 7/1935 | Fed. Rep. of Germany | 424/172 |
| 750764 | 1/1945 | Fed. Rep. of Germany | 424/172 |
| 875525 | 3/1953 | Fed. Rep. of Germany | 424/319 |
| 884991 | 7/1953 | Fed. Rep. of Germany | 424/319 |
| 1518665 | 2/1968 | France | 424/358 |
| 675152 | 7/1952 | United Kingdom | 424/172 |
| 1109511 | 4/1968 | United Kingdom | 424/172 |
| 1439403 | 6/1976 | United Kingdom | 424/319 |

*Primary Examiner*—Dale R. Ore
*Attorney, Agent, or Firm*—Forrest L. Collins; Patrick J. Span

[57] ABSTRACT

The present invention discloses a self-emulsifying cosmetic base having a unique ability to form oil-in-water emulsions.

8 Claims, No Drawings

SELF-EMULSIFYING COSMETIC BASE

BACKGROUND OF THE INVENTION

1. Field of the Invention

The present invention relates to forming emulsions such as are commonly used in the cosmetic industry.

2. Description of the Art

Nitrogen containing amphoteric surfactants such as those utilized in the present invention are described in U.S. Pat. No. 2,816,920 issued to Anderson on Dec. 17, 1957. Disclosures of related amphoteric surfactants include U.S. Pat. No. 3,430,641 issued Mar. 4, 1969 to Newman. Further disclosures of such materials are found in U.S. Pat. No. 2,929,788 issued Mar. 22, 1960 to Freese et al.

Related compounds for use in cosmetic compositions such as shaving soaps and shampoos are disclosed in U.S. Pat. No. 2,468,012 issued to Isbell on Apr. 10, 1949. Similar related compounds are disclosed in U.S. Pat. No. 2,814,643 issued to Aelony on Nov. 26, 1957.

A later U.S. Patent to Freese, No. 3,093,591 issued June 11, 1963 discloses the use of mixtures of amphoteric surfactants as are employed in the present invention. An interesting disclosure of two-phase liquid detergent compositions is found in U.S. Pat. No. 3,533,955 issued Oct. 13, 1970 to Pader et al.

Various cosmetic formulations containing fatty alcohols and/or nitrogen containing amphoteric surfactants are disclosed in COSMEDIA ® Product Sheets FC-5, HB-4, HB-5, MB-1 and SC-1 available from the Cosmedia group of General Mills Chemicals, Inc. The foregoing formulation sheets demonstrate the need for self-emulsifying cosmetic bases.

Throughout the specification and claims, percentages and ratios are by weight unless otherwise indicated. Temperatures are indicated by degrees Celsius unless otherwise stated.

SUMMARY OF THE INVENTION

A solid form cosmetic base having self-emulsifying properties is prepared comprising:
(a) a compound of the formula:

MOOCCH$_2$CH$_2$NRCH$_2$CH$_2$COOM wherein R is a fatty alkyl, and;
(b) a saturated fatty alcohol
wherein the weight ratio of component (a) to component (b) is from about 1/10:1 to about 2/13:1 and M is selected from the group consisting of salt forming cations and hydrogen in a respective weight ratio of from about 1:10$^0$ to about 1:10$^{-10}$.

The foregoing self-emulsifying cosmetic base is found to have low energy input requirements in preparing the cosmetic base and correspondingly low energy requirements to form the emulsified cosmetic base upon the addition to oil and water.

DETAILED DESCRIPTION OF THE INVENTION

As it was noted above, the present invention deals with a self-emulsifying cosmetic base. By definition the term self-emulisfying means that the cosmetic base is made up of more than one material which alone would not serve to emulsify a mixture of oil and water. However, due to the unique combination of the materials in this self-emulsifying cosmetic base, it is possible to form an emulsion from oil and water upon addition of the self-emulsifying cosmetic base.

It has been found that the combination of a self-emulsifying cosmetic base to oil and water to form an emulsion does so more efficiently at lower energy costs than if the two ingredients in the self-emulsifying cosmetic base are separately added to the oil and water.

It has been found that emulsions formed at the lower temperatures using the self-emulsifying cosmetic base are considerably more stable than high temperature emulsions formed by separately combining the ingredients. By way of theory it is believed that once an emulsion is obtained any further energy input can cause the emulsion to become unstable. That is, one may not routinely heat a mixture which is in the process of becoming an emulsion to any particular higher temperature followed by lowering the temperature of the emulsion and expect the same properties to be present in that emulsion as are present in a similar emulsion not heated to the higher temperature.

It has therefore been found in the present invention that the composition so formed is unique in that it allows two materials, neither of which will emulsify a water and oil system alone, to be prepared in a solid form for convenient use by the cosmetic manufacturer.

Secondly, the energy requirements for preparing an oil-in-water emulsion from the solid form cosmetic base comprising only the nitrogen containing amphoteric surfactant and the fatty alcohol are considerably lower than by forming an emulsion through random addition of the various ingredients. Moreover, emulsions formed from the composition of the present invention tend to be more stable than similar emulsions formed in other ways.

The first component to be discussed in forming the solid form cosmetic base is the nitrogen containing amphoteric surfactant. The nitrogen containing amphoteric surfactant is a compound of the formula:

MOOCCH$_2$CH$_2$NRCH$_2$CH$_2$COOM wherein M is a member selected from the group consisting of salt forming cations and hydrogen. The weight ratio of the salt forming cation to the hydrogen should be from about 1:10$^0$ to about 1:10$^{-10}$, preferably 1:10$^{-1}$ to about 1:10$^{-9}$, most preferably from about 1:10$^{-2}$ to about 1:10$^{-8}$. R is a fatty alkyl radical as later described.

Said otherwise, the nitrogen containing amphoteric surfactant must contain the salt forming cation and hydrogen in a particular ratio such that when one mole of the nitrogen containing amphoteric surfactant dissolved in a liter of water would exhibit a pH between about 2.5 and 9.5.

It has been conveniently found that the ratio of the salt forming cation to the hydrogen value of M provides a beneficial effect in emulsifying water and oil for the cosmetic product. That is, at least a portion of the self-emulsifying property of the solid form cosmetic base is due to the particular balance of the salt forming cation and hydrogen in the nitrogen containing amphoteric surfactant.

Preferably the salt forming cation is a member selected from the group consisting of sodium, potassium, ammonium and substituted ammonium derivatives and mixtures thereof. By substituted ammonium derivatives the class of materials therein includes lower alkyl (C$_{1-3}$) derivatives of ammonium either fully or partially replacing the hydrogen substituents on the ammonium. Most preferably the salt forming cation is sodium.

The value of R in the nitrogen containing amphoteric surfactant should be from about 10 to about 24, preferably 12 to 20 and most preferably from about 12 to about 18 carbon atoms in length. R is preferably naturally derived such as from beef stock or coconut oil thereby having a large amount of lauryl, myristyl, cetyl and stearyl radicals present.

The second component in the solid form cosmetic base is a saturated fatty alcohol. Preferably the fatty alcohol contains from about 10 to about 24 carbon atoms, most preferably from about 12 to about 18 carbon atoms. It is also highly desirable that the saturated fatty alcohol be monohydric to ensure a high degree of stability when forming an emulsion. More preferably the natural alcohols are commensurate with the naturally derived groups of the nitrogen containing amphoteric surfactant, i.e. each having the same number of carbon atoms.

The solid form cosmetic base contains the nitrogen containing amphoteric surfactant and the saturated fatty alcohol in a respective weight ratio of from about 1/10:1 to about 2/13:1, preferably from about 1/9:1 to about 1/7:1.

It has also been found that by combining the materials of the present invention to form the self-emulsifying cosmetic base that considerably less amounts of the nitrogen containing amphoteric surfactant are required thereby lowering the cost of that component in the finished cosmetic product with no loss in the effectiveness of the emulsifying properties.

Additional components which may be included with the self-emulsifying cosmetic base but which are not required include all manner of cosmetic ingredients such as perfumes, water, emollients, surfactants, humectants, and other skin or hair conditioning ingredients.

The components of the present invention are combined to form the self-emulsifying cosmetic base by warming the fatty alcohol component to about 75 degrees C until it becomes clear and completely melted and then separately heating the nitrogen containing amphoteric surfactant to 70 degrees C. It should be recognized immediately that the only reason for heating the normally liquid nitrogen containing amphoteric surfactant is to ensure that it is thoroughly dispersed in the fatty alcohol.

It has been found best to add the nitrogen containing amphoteric surfactant to the fatty alcohol with continuous agitation i.e., mild shear conditions until the mixture turns completely clear. Thereafter, the mixture of the nitrogen containing amphoteric surfactant and the fatty alcohol are cooled and prepared in any solid form desired such as block, granule, flake or powdered form.

The following exemplifies the present invention.

EXAMPLE I 30 parts of Deriphat ® 160C (30% active) available from Henkel Corporation, a nitrogen containing amphoteric surfactant, wherein R contains 12 carbon atoms as shown in the structural formula in the Summary of the Invention and having an approximate ratio of sodium atoms to hydrogen atoms of 9 to 10, is heated to 70 degrees C. Cetyl alcohol at 80 parts is heated to 75 degrees C until clear and completely melted. The Deriphat ® 160C is then added to the alcohol with continuous agitation provided by a "Lightin" blender until the mixture turns completely clear.

The self-emulsifying cosmetic base is then allowed to cool to a solid form and flaked to a consistency of particles having approximate dimensions of 3 mm by 8 mm by 2 mm.

The above example may be repeated using alcohols having a carbon chain length of from about 14 to about 18.

Potassium, ammonium or a triethyl ammonium derivative may be substituted for sodium in the above example. Similarly, the weight ratio of the salt forming cation to the hydrogen in the nitrogen containing surfactant may be varied between 1:1 to $1:10^{-10}$ with substantially similar results obtained. The products of this Example may also be prepared by spray-drying.

EXAMPLE II

The self-emulsifying cosmetic base of Example I is utilized by incorporating it into a hand and body lotion.

The hand and body lotion is prepared having a nominal composition of:

|  | PARTS |
|---|---|
| Light Mineral Oil | 5.0 |
| Generol ® 122E5 | 2.0 |
| (Hensel Corporation) | |
| (PEG-5 Soya Sterol) | |
| Stearic acid XXX | 3.0 |
| Cetyl alcohol | 3.2 |
| Generol ® 122E10 | 0.5 |
| (PEG-10 Soya Sterol) | |
| Deriphat ® 160C (sodium | 0.4 |
| Lauriminodipropionate as 100% | |
| solids) | |
| Glycerine | 2.5 |
| Sorbitol | 2.5 |
| Water | to 100 |

The foregoing hand and body lotion is prepared by combining the remaining components at 60 degrees C with the self-emulsifying cosmetic base at 65 degrees c with moderate agitation. The amount of self-emulsifying cosmetic base is at 3.6 parts.

The foregoing provides an ideal hand and body lotion utilizing less of the nitrogen containing amphoteric surfactant than was previously known to be useful in forming the emulsion.

EXAMPLE III

A make-up base is formed by combining 6.75 parts of the self-emulsifying cosmetic base of Example I into the following formula:

|  | PARTS |
|---|---|
| Generol ® 122E25 | 10.0 |
| (PEG-25 Soya Sterol) | |
| Generol ® 122E5 | 2.0 |
| (PEG-5 Soya Sterol) | |
| Mineral Oil, light | 4.0 |
| Isopropyl myristate | 2.0 |
| Cetyl/stearyl alcohol (1:1) | 6.0 |
| Deriphat ® 160C (Sodium | 0.75 |
| Lauraminodipropionate as 100% | |
| solids) | |
| Propylene glycol | 8.0 |
| Water, deionized | to 100 |

The composition is prepared by heating the self-emulsifying cosmetic base to 75 degrees C and heating the remaining components to 70 degrees C and adding the self-emulsifying cosmetic base thereto.

The make-up base may be utilized alone as described or may have other materials added to it such as pigments including Whittaker #141 Alpine Talc, U.S.P., Titanium dioxide and iron oxides. The inclusion of the pigmentation ingredients is best accomplished at temperatures higher than that utilized above thus the primary make-up base should be heated to about 90 degrees C to incorporate the pigments.

What is claimed is:

1. A solid form cosmetic base having self-emulsifying properties consisting of:
   (a) a compound of the formula:

MOOCCH$_2$CH$_2$NRCH$_2$CH$_2$COOM where R is a fatty alkyl having from about 10 to about 24 carbon atoms, and;
   (b) a saturated fatty alcohol having from about 10 to about 24 carbon atoms
   wherein the weight ratio of component (a) to component (b) is from about 1/10:1 to about 2/13:1 and M is selected from the group consisting of salt forming cations and hydrogen in a respective weight ratio of from about $1:10^0$ to about $1:10^{-10}$.

2. The cosmetic base of claim 1 wherein the weight ratio of component (a) to component (b) is from about 1/9:1 to about 1/7:1.

3. The cosmetic base of claim 1 wherein the salt forming cation portion of M is selected from the group consisting of sodium, potassium, ammonium and substituted ammonium derivatives and mixtures thereof.

4. The cosmetic base of claim 1 wherein the fatty alcohol contains from about 12 to about 18 carbon atoms.

5. The cosmetic base of claim 1 wherein component (a) contains the salt forming cation to the hydrogen in a respective weight ratio of from about $1:10^{-1}$ to about $1:10^{-9}$.

6. The cosmetic base of claim 1 wherein R contains from about 12 to about 18 carbon atoms.

7. The cosmetic base of claim 3 wherein M is sodium.

8. The cosmetic base of claim 1 wherein R and the fatty alcohol contain the same number of carbon atoms.

* * * * *